(12) United States Patent
Lam et al.

(10) Patent No.: US 11,152,197 B2
(45) Date of Patent: Oct. 19, 2021

(54) METHOD OF DETERMINING CELL CYCLE STAGE DISTRIBUTION OF CELLS

(71) Applicant: City University of Hong Kong, Kowloon (HK)

(72) Inventors: Yun Wah Lam, North Point (HK); Hong Juan Dong, Shanghai (CN)

(73) Assignee: City University of Hong Kong, Kowloon (HK)

( * ) Notice: Subject to any disclaimer, the term of this patent is extended or adjusted under 35 U.S.C. 154(b) by 260 days.

(21) Appl. No.: 14/748,523

(22) Filed: Jun. 24, 2015

(65) Prior Publication Data
US 2016/0379811 A1 Dec. 29, 2016

(51) Int. Cl.
| | |
|---|---|
| *H01J 49/00* | (2006.01) |
| *H01J 49/40* | (2006.01) |
| *H01J 49/16* | (2006.01) |
| *G01N 33/487* | (2006.01) |

(52) U.S. Cl.
CPC .... *H01J 49/0027* (2013.01); *G01N 33/48707* (2013.01); *H01J 49/164* (2013.01); *H01J 49/40* (2013.01)

(58) Field of Classification Search
CPC ...... H01J 49/40; H01J 49/164; H01J 49/0027; G01N 33/48707
See application file for complete search history.

(56) References Cited

U.S. PATENT DOCUMENTS

2011/0208433 A1* 8/2011 Grigorieva ....... G01N 33/57415
702/19

OTHER PUBLICATIONS

Kim, Chongtae, et al. "Regulation of post-translational protein arginine methylation during HeLa cell cycle." Biochimica et Biophysica Acta (BBA)-General Subjects 1800.9 (2010): 977-985.*
Kim, Chongtae, et al. "Regulation of post-translational protein arginine methylation during HeLa cell cycle." Biochimica et Biophysica Acta (BBA)-General Subjects 1800.9 (2010): Supplementary Materials: p. 1-9. (Year: 2010).*
Breindl, M., and D. Gallwitz. "Effects of cordycepin, hydroxyurea and cycloheximide on histone mRNA synthesis in synchronized HeLa cells." Molecular biology reports 1.5 (1974): 263-268.*
Decker, Emily D., et al. "Proteomic analysis of differential protein expression induced by ultraviolet light radiation in HeLa cells." Proteomics 3.10 (2003): 2019-2027.*

(Continued)

*Primary Examiner* — Robert J Eom
(74) *Attorney, Agent, or Firm* — Renner, Kenner, Greive, Bobak, Taylor & Weber

(57) ABSTRACT

A method of determining a cell cycle stage distribution of cells includes the steps of providing a cell sample; pre-treating the cell sample with a solvent; mixing the pre-treated cell sample with a matrix solution to obtain a mixture solution; depositing the mixture solution on a sample plate; obtaining a mass spectrum analysis of the deposited mixture solution; and identifying at least two marker peaks from the mass spectrum analysis, wherein a ratio between the marker peaks provides information about a cell cycle stage distribution of the cell sample, wherein the mass spectrum analysis is a matrix-assisted laser desorption/ionization time-of-flight mass spectrum test.

7 Claims, 9 Drawing Sheets
(9 of 9 Drawing Sheet(s) Filed in Color)

(56) References Cited

OTHER PUBLICATIONS

Qiu, Junzhuan, et al. "Cell cycle-dependent and DNA damage-inducible nuclear localization of FEN-1 nuclease is consistent with its dual functions in DNA replication and repair." Journal of Biological Chemistry 276.7 (2001): 4901-4908. (Year: 2001).*

* cited by examiner

METHOD OF DETERMINING CELL CYCLE STAGE DISTRIBUTION OF CELLS

TECHNICAL FIELD

The present invention relates to a method of determining cell cycle stage distribution of cells, and more particularly to determine the cell cycle stage distribution in a population of mammalian cells.

BACKGROUND

Determination of cell activities, such as cell cycle, cell viability and cell differentiation, in response to treatments has numerous applications and is of great commercial value. In developing anticancer drugs, it is crucial to define cell cycle physiology accurately and rapidly so as to better understand the effect of the anti-cancer drugs on normal or cancerous cells.

A variety of techniques are currently available to estimate the drug-induced alteration of cell cycle stage distribution. Flow cytometry, western blotting and time-lapse live-cell microscopy are the commonly used techniques for determining the cell cycle stage distribution of cells. However, these techniques usually involve complex and tedious procedures with multiple steps, making these techniques incompatible with high throughput screening platforms. For example, the measurement of DNA content by flow cytometry analysis for cell cycle determination requires multiple steps of washing, fixing and staining of the cells. The entire analysis requires lengthy and complicated experimental procedures.

SUMMARY OF THE INVENTION

Matrix-assisted laser desorption/ionization time-of-flight mass spectrometry (MALDI TOF MS) has been recently adopted to identify bacteria and fungi. It can detect and identify high molecular weight compound, particular peptides, proteins, oligonucleotide, and oligosaccharides. However, there is currently a lack of well-established protocol for applying this technology to measure cell activities, especially the cell cycle stage distribution, of mammalian cells. Accordingly, there remains a need for better cell analytic methods for mammalian cells.

However, the inventors have used this technique on mammalian cells with unexpected results. Specifically, the inventors have optimized the method of using MALDI TOF MS for determining specific cell activities or determining the cell cycle stage distribution of mammalian cells to provide a more informative mass spectrum for subsequent analysis. The enhanced mass spectrum is of great value in investigating the cellular activities, as well as the mechanism behind. The inventors have also derived a strategy to identify a biomarker for determining the cell cycle stage distribution of cells by using MALDI TOF MS.

According to a first aspect of the present invention, there is provided a method of determining a cell cycle stage distribution of cells, comprising the steps of: providing a cell sample; pre-treating the cell sample with a solvent; mixing the pre-treated cell sample with a matrix solution to obtain a mixture solution; depositing the mixture solution on a sample plate; obtaining a mass spectrum analysis of the deposited mixture solution; and identifying at least two marker peaks from the mass spectrum analysis, wherein a ratio between the marker peaks provides information about a cell cycle stage distribution of the cell sample, wherein the mass spectrum analysis is a matrix-assisted laser desorption/ionization time-of-flight mass spectrum test.

According to a second aspect of the present invention, there is provided a method of identifying a biomarker corresponding to a cell cycle stage distribution of cells, comprising steps of: conducting a matrix-assisted laser desorption/ionization time-of-flight mass spectrometry test for cells to obtain a mass spectrum analysis of the cells; and identifying at least two marker peaks from the mass spectrum analysis, and defining a ratio between the marker peaks, wherein the ratio is a biomarker providing information about a cell cycle stage distribution of the cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present invention will now be described, by way of example, with reference to the accompanying drawings in which.

DETAILED DESCRIPTION

Figure 1B:
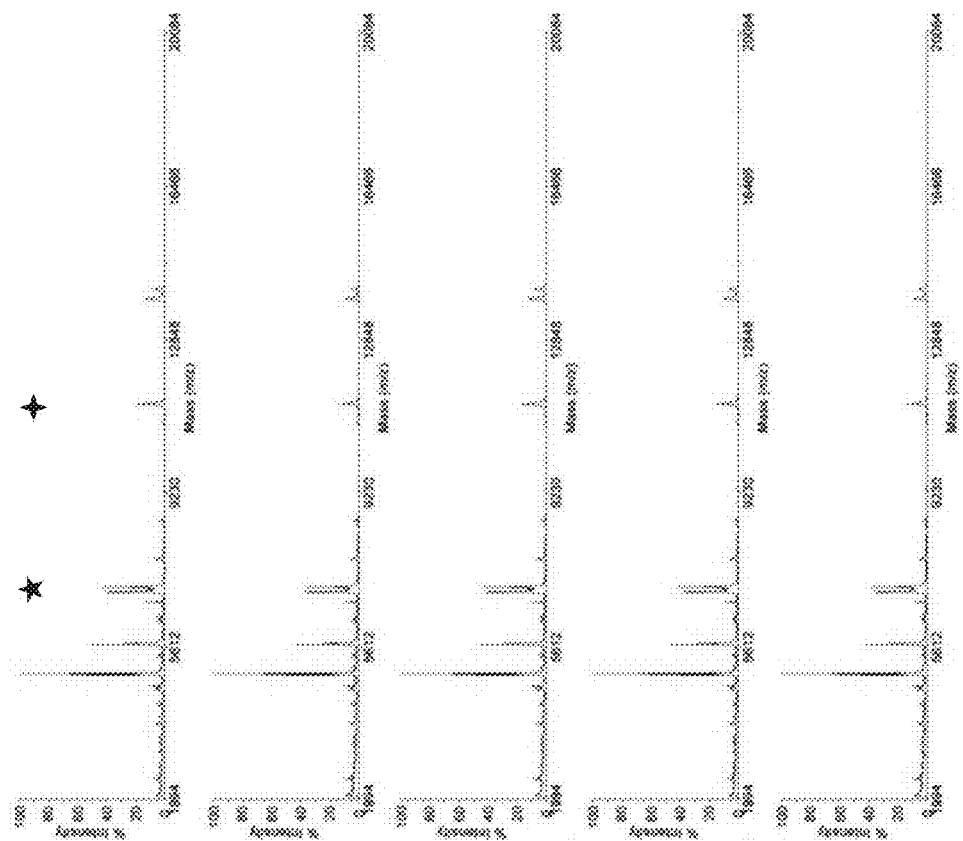
FIG. 1b shows MALDI TOF mass spectra of HeLa cell lysate.

Matrix-assisted laser desorption/ionization time-of-flight mass spectrometry (MALDI TOF MS) is applied in the analytical field to yield specific peaks and spectra for different analytes such as protein and yeast. There are two main steps in MALDI TOF MS. The first step is embedding an analyte in an organic solvent called matrix. The matrix comprises ultra-violet (UV) laser sensitive molecules which absorb energy from the laser. Then, under a vacuum condition, the second step is carried out by firing the UV laser to the matrix. The matrix absorbs the energy and causes the matrix crystals to desorb and sublime into gas phase. During this step, the analyte is ionized by the matrix molecules. Under a high voltage, the ionized analyte is accelerated and moves to a detector. The detector analyzed the ions received. The higher the mass of ion is, the longer the required time of flight. As a result, ions are detected by their masses. Analyzing the mass spectrum obtained allows a user to characterize the tested subject for further studies like protein expression profiles and cell viability, for example, after treatments. However, there are currently very few standardized protocols available for conducting MALDI TOF MS test in mammalian cells for detecting a specific cell activity, in particular no standardized protocol for determining the cell cycle stage distribution in mammalian cells.

Accordingly, one aspect of the present invention is to provide an improved method of using MALDI TOF MS to determine the cell cycle stage distribution, in particular, to determine the cell cycle stage distribution in a mammalian cell population. The method can be applied to intact cells or a cell lysate for determination.

In the present invention, there is provided a method of determining the cell cycle stage distribution of cells, comprising the steps of: providing a cell sample; pre-treating the cell sample with a solvent; mixing the pre-treated cell sample with a matrix solution to obtain a mixture solution; depositing the mixture solution on a sample plate; obtaining a mass spectrum analysis of the deposited mixture solution; and identifying at least two marker peaks from the mass spectrum analysis, wherein a ratio between the marker peaks provides information about the cell cycle stage distribution of the cell sample, wherein the mass spectrum analysis is a matrix-assisted laser desorption/ionization time-of-flight mass spectrum test.

Without intending to be limited by theory, it is believed that MALDI TOF MS can detect a range of cell activities and provide information regarding the property of a cell population, such as cell cycle stage distribution, apoptosis, cell differentiation and protein expression. In a preferred embodiment of the present invention, the method determines the cell cycle stage distribution in a cell sample. The cell sample may be an intact cell sample or a cell lysate sample prepared from mammalian cells, plant cells or prokaryotic cells.

In one example of the present invention, the cell sample is a cell lysate of cervical cancer cells HeLa. To prepare the HeLa cell lysate sample, HeLa cell line was firstly obtained from ATCC and then grown as adherent mono-layers in Dulbecco's modified Eagle's medium, supplemented with 10% fetal bovine serum and antibiotics (all from Invitrogen, Carlsbad, Calif.), in a humidified atmosphere of 5% carbon dioxide and 95% air at 37° C. After incubation or treatment, the cells were collected by trysinization and washed with 10 ml cold phosphate buffered saline (PBS) thrice. The collected cells were spun into a cell pellet and immediately frozen at 80° C. for storage. When in use, the cell pellet was thawed and diluted with a solvent and subjected to a sonication for cell lysis on ice. Finally, a cell sample of HeLa cell lysate was obtained for MALDI TOF MS test. A cell lysate sample is advantageous in that it can provide a more informative mass spectrum. It is because a complete cell lysis allows the release of intra-cellular molecules of the cells for subsequent ionization and detection during the test.

Alternatively, intact cells may also be used in the MALDI TOF MS test (MS test). The advantages of using intact cells in the test are that no further treatment is required after the cell collection, and the results obtained can reveal the freshly harvested cell status.

Figure 1A:
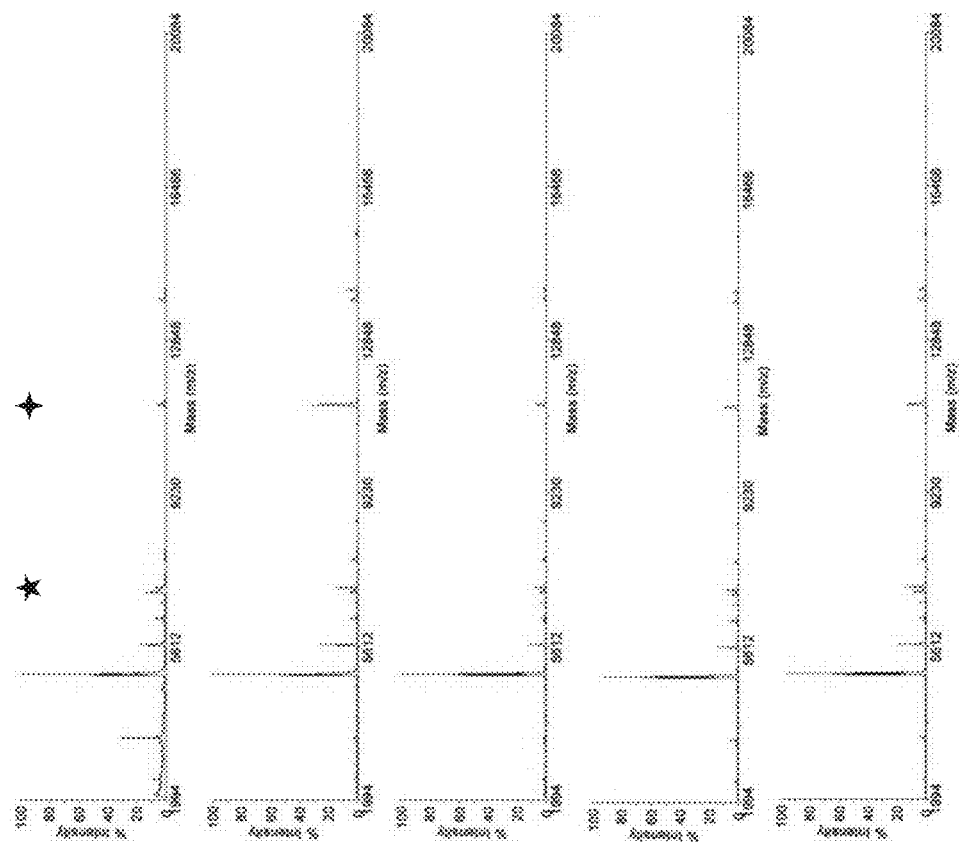
FIG. 1a shows MALDI TOF mass spectra of intact HeLa cells.

With reference to FIGS. 1a and 1b, there are the MS test results obtained from analyzing HeLa intact cells and HeLa cell lysate respectively. FIG. 1a refers to the results of HeLa intact cells and FIG. 1b refers to the results of HeLa cell lysate. It is obvious that the cell lysate gave mass spectra with a stronger intensity. The detected peaks shown in the intact cell mass spectra are generally low in relative intensity. There are also some fluctuating peaks in the intact cell mass spectra. Specifically, referring to the peak marked with "✦", this peak is generally stable in the cell lysate mass spectra but is fluctuating in the intact cell mass spectra. Moreover, the peak marked with "★" in the cell lysate mass spectra gave a stronger signal than that in intact cell mass spectra. Accordingly, the cell lysate sample can generate a stronger signal and results in higher reproducibility mass spectra than that of intact cell. Therefore, preferably, a cell lysate is used in the present invention.

The cell sample of the present invention is pre-treated before mixing with the matrix solution. Pre-treatment of the cell sample is necessary as it significantly improves the mass spectrum obtained. More characteristic peaks may be revealed through pre-treatment such that a marker peak can be easily identified. In this embodiment, the cell sample is pre-treated with a solvent before mixing with the matrix solution for the MS test. Preferably, the solvent is PBS or purified water. PBS is a well-known physiological buffer for cells, which provides a constant pH static environment for cells and minimizes any cellular changes in the frozen cells. Purified water such as Milli-Q water is substantially free from salt and buffer. As such, when the purified water is used as the solvent to re-suspend the cell lysate pellet or pre-wash the intact cells, no salts or buffer is left to affect the sensitivity of the detector towards the analyte during the MS test.

Figure 2A:
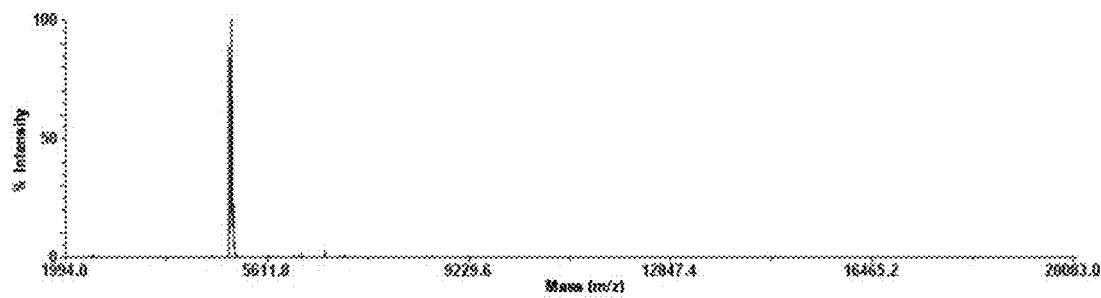
FIG. 2a is a MALDI TOF mass spectrum of HeLa cell lysate pre-treated with PBS.

In this example, three pre-treatment approaches were tested to pre-treat the HeLa cell lysate sample before conducting the MS test. The first approach makes use of PBS as a diluent or solvent for preparing a cell suspension. The frozen HeLa cell lysate was re-suspended with PBS to prepare a cell suspension for the MS test. The cell suspension was mixed with the matrix solution to form a mixture solution. The mixture solution was then deposited on a sample spot on a target plate with an additional matrix solution (e.g. 0.5 ul) added on the loaded sample spot. FIG. 2a shows the MS test results obtained from the first approach. Apparently, no detailed mass spectrum can be obtained and such a mass spectrum does not reveal any meaningful peak for further evaluation. As mentioned before, it is believed that PBS prevents significant physiological changes of the cells. However, PBS contains salts and buffer molecules. Salts and buffer molecules may hinder the energy transfer from the matrix to the cell lysate or increase the energy required to trigger the lysate ions to fly towards the detector. As a result, no meaningful peaks were obtained from the first approach.

Figure 2B:
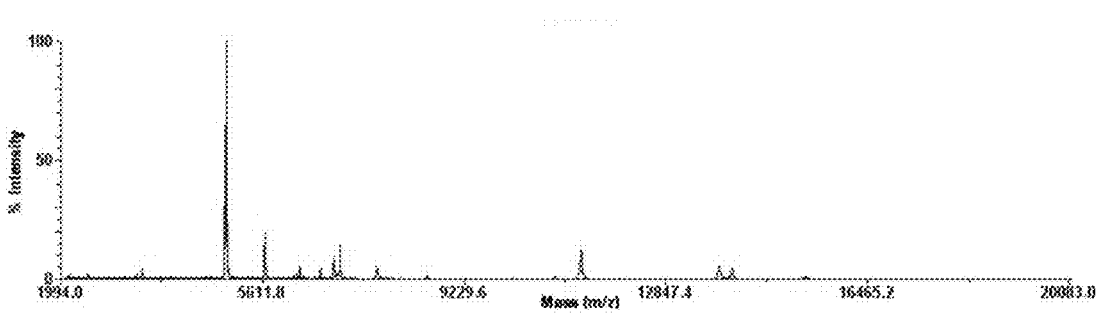
FIG. 2b is a MALDI TOF mass spectrum of HeLa cell lysate pre-treated PBS and washed with TFA.

The second approach is to enhance the performance of the cell sample when compared with the first approach. In this example, the cell lysate was washed on the sample spot before the addition of the matrix solution. Since the sample matrix is organic while salt and buffer are inorganic, trifluoroacetic acid (TFA), e.g. 0.1% TFA, was used as a washing agent to dissolve buffer in the cell suspension prepared according to the first approach. TFA would not dissolve the matrix and therefore it was introduced to wash the mixture solution after the loaded mixture solution on the sample spot was air-dried. This was surprisingly found to be advantageous in that it is believed that the TFA is able to remove or reduce the amount of salts and buffer molecules in the mixture solution. As a result, the second approach may be able to obtain an even better mass spectrum compared with the first approach. With reference to FIG. 2b, the washed mixture solution improved the mass spectrum by expressing more peaks after 5000 Da. However, this expression is still very weak. One possible reason may be that the cell lysate fragments in the cell suspension were not totally embedded in the matrix. Therefore, when TFA was flushed into the mixture solution on the sample spot deposited on the target plate, some cell lysate fragments might be washed away. This causes an irreversible lost of lysate and affects the quality of mass spectrum generated.

Figure 2C:
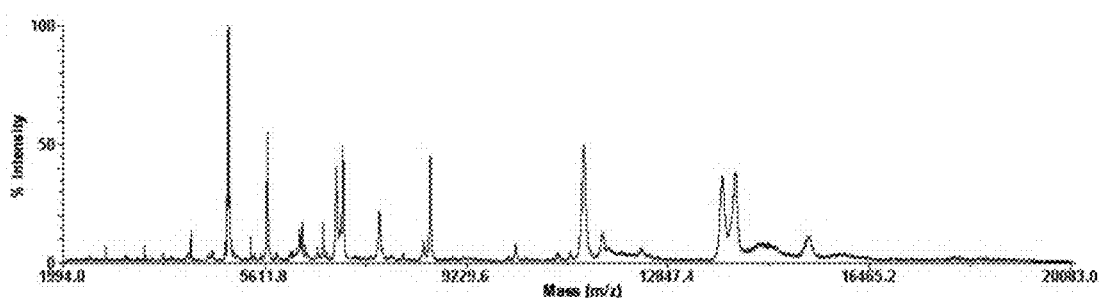
FIG. 2c is a MALDI TOF mass spectrum of HeLa cell lysate pre-treated with Milli-Q water.

Accordingly, a third approach was tested to improve the above defects. For the third approach, purified water is used to re-suspend the cell lysate to prepare the cell suspension. Specifically, Milli-Q water was added to re-suspend the frozen HeLa cell lysate. Since Milli-Q water is substantially free from salts and buffer molecules, no further washing step is required. Accordingly, the cell lysate content can be maintained while minimize the effect of salts and buffer molecules in the mixture solution for MS test. With reference to FIG. 2c, more significant peaks are observed. Therefore, preferably, purified water is used to pre-treat the cell sample in the present invention so as to obtain a more informative mass spectrum for further analysis.

The matrix solution of the present invention consists of crystallized molecules that are able to ionize the analyte when they absorb energy from the laser. It has surprisingly been found that different matrix solutions can be tailored to suit the individual needs of the researcher. Preferably, the matrix solution may be a solution formed by at least one of the following compounds: 3,5-dimethoxy-4-hydroxycinnamic acid, α-cyano-4-hydroxycinnamic acid (CHCA), 2,5-dihydroxybenzoic acid (DHB), trifluoroacetic acid (TFA) and acetonitrile (ACN). In this example, the matrix solution is a solution of CHCA diluted in ACN/aqueous 0.1% TFA (7/3, v/v). A person skilled in the art would understand that other possible alternatives can also be applied in this invention to ionize the analyte for detection.

The matrix solution is then mixed with the cell sample or the pre-treated cell sample for loading on the sample spot of the target plate for analysis. In this example, a sandwich method is applied to mix the matrix solution with the cell sample to form the mixture solution, as well as to load the mixture solution on the sample spot. Specifically, HeLa cell lysate and matrix solution were placed into a microtube with volume ratio 1:1 and mixed well, the mixture solution was left for 3 minutes in room temperature for reaction. 1 uL of the mixture solution was deposited onto the MALDI target (target plate), and the solvent was evaporated at room temperature. Another drop of the matrix solution was further added on the target plate. Such a loading can be conducted by automated spotting or manual spotting. In automated spotting, the mixture solution may be loaded in a syringe, and wherein the syringe is connected to a pump such that the mixture solution is uniformly distributed on the sample plate. In manual operation, a pipette is used to spot the mixture solution in a careful manner. Alternatively, other commonly known method can also be applied to load the cell sample and the matrix on the target plate for detection.

In a preferred embodiment of the present invention, the method is conducted to determine the cell cycle stage distribution of a cell sample. To accurately evaluate the cell cycle stage distribution of cells, synchronization is required to make sure all the cells in the cell sample are arrested at the same phase for detection. This is particularly useful to evaluate the change of DNA content in the cells with respect to different cell cycle stage by using flow cytometry and compare the results with the MS test to identify the marker peak of different cell cycle stages of the cell. Accordingly, the method of the present invention further comprises the steps of detecting the DNA content of the cell sample by using a flow cytometer and comparing the DNA content with the mass spectrum analysis.

Regarding the synchronization, various synchronizing approaches may be applied, e.g. inhibiting the DNA synthesis of the cells by using inhibitors such as thymidine, aminopterin and hydroxyurea, as well as eliminating nutrients from the culture medium to starve the cells for about 24 hours.

Figure 3:
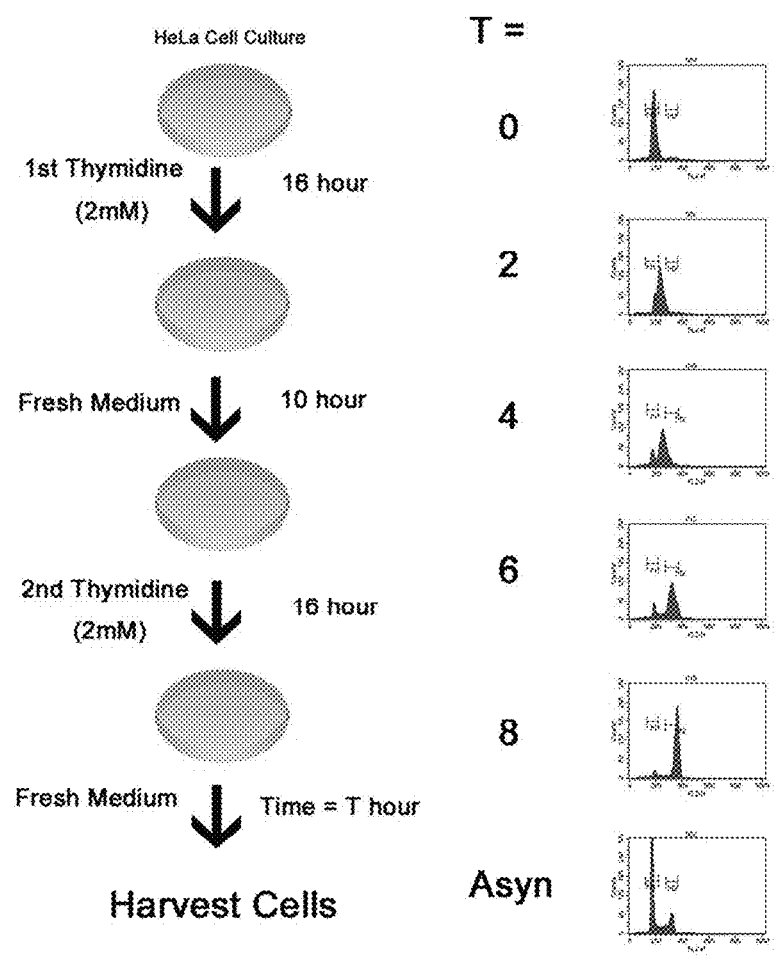
FIG. 3 shows a schematic diagram of a synchronization step with reference to the results obtained in a flow cytometry in accordance with one embodiment of the present invention.

In an example herein, a double thymidine block synchronization procedure may be used. FIG. 3 illustrates a schematic diagram of double thymidine block synchronization on HeLa cells. HeLa cells were first synchronized by the classical double thymidine block procedure, in which thymidine was added to a cell culture medium to induce an imbalanced intracellular nucleotide pool. Accordingly, the DNA synthesis of HeLa cells was hindered, and the cells are arrested at the G1-S junction as mentioned by Hyland et al. (Hyland, P. L., Keegan, A. L., Curran, M. D., Middleton, D., McKenna, P. G., & Barnett, Y. A. (2000). Effect of a dCTP:dTTP pool imbalance on DNA replication fidelity in Friend murine erythroleukemia cells. Environ. Mol. Mutagen, 36, 97-96). By removing the exogenous thymidine, this block was reversed, and cells were then allowed to proceed through the cell cycle in synchrony. Cells were subjected to two blockings in order to ensure all cells were synchronized at G1/S phase. When the block is released, the cells propagate from G1 to S and then G2 together. Thus, harvesting cells in different time points can collect cells at the desired cell cycle stage for analysis.

FIG. 3 shows that six HeLa cells cultures were incubated. All HeLa cell cultures came from the same parental dish. After 24 hours of cell seeding, 2 mM of thymidine was introduced to five of the cultures and incubated at 37° C. while the remaining one represents an asynchronized cell sample. After 16 hours, the cell cultures were washed with PBS thrice so as to remove thymidine and the cell cultures were therefore released from the first thymidine block for 10 hours by replacing the culture medium with a fresh DMEM medium. Next, another addition of 2 mM of thymidine was introduced to the cell cultures to trigger the second blocking. The second blocking lasted for 16 hours. The cell cultures were then washed with PBS thrice and were refreshed by the fresh medium. At indicated time points e.g. 0, 2, 4, 6 and 8 hr, the cell cultures were harvested for further analysis in flow cytometry.

In this example, the harvested cells were fixed by 70% ice cold ethanol and followed by staining with 2.5 ug/ml of propidium iodide (PI). PI is a nucleic acid label that, in the presence of RNase, marks and gives DNA fluorescence. DNA content of cells acts as a reference of cell cycle stages in fluorescence-activated cell sorting (FACS) analysis. As shown in FIG. 3, when T=0 hr, most of the cells were at G1 phase (DNA content is 2n). This indicated that double thymidine block successfully hindered the DNA synthesis of the cells and arrested the cells at G1/S phase. When time passes by, the DNA content of the cells moves from 2n to 4n. Accordingly, this reveals that HeLa cells collected at different time points were cell cycle specific.

Figure 4:
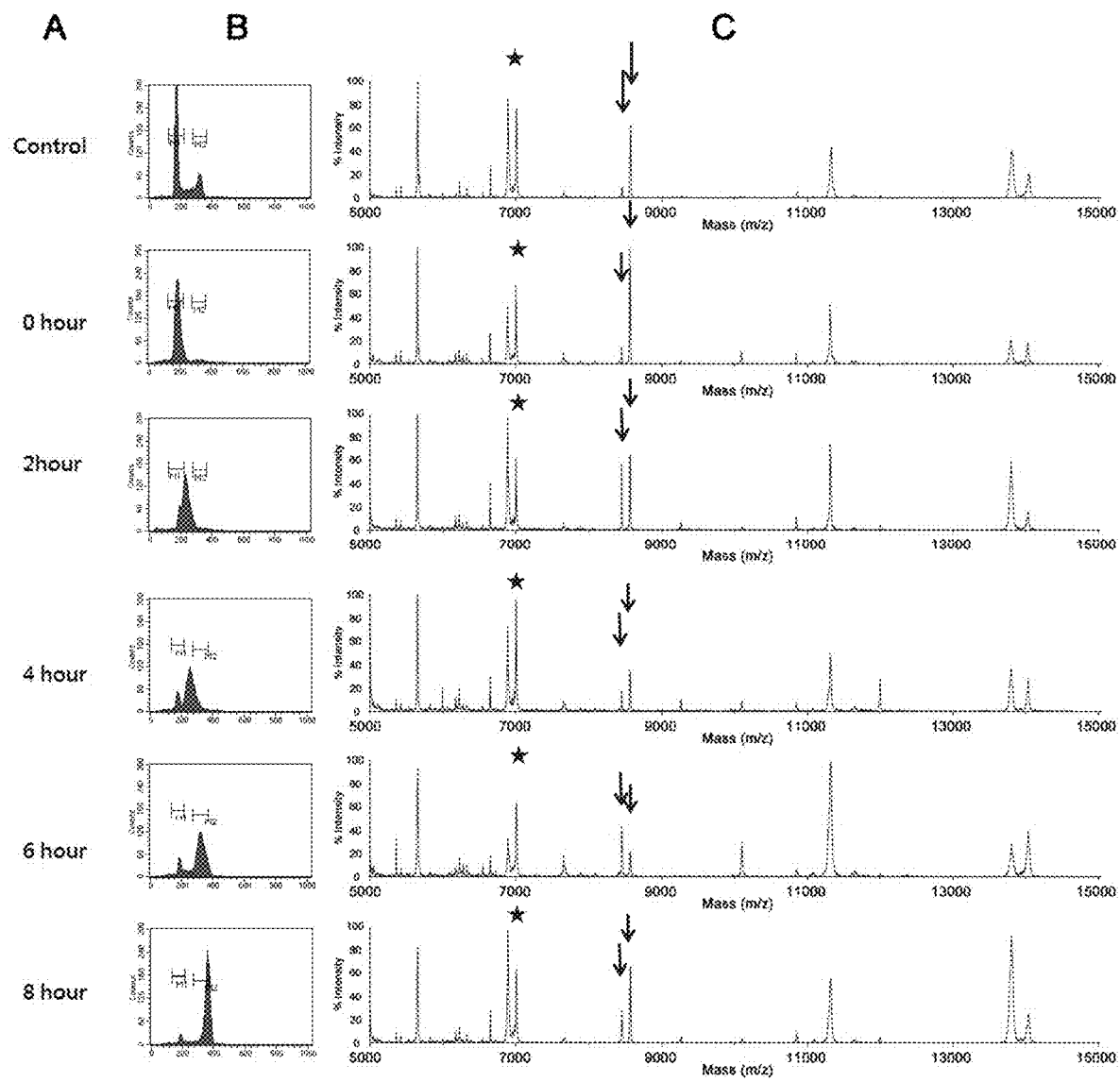
FIG. 4 shows DNA profiles of the cell samples in one embodiment of the present invention as measured in flow cytometry and the corresponding MALDI TOF mass spectra.

With reference to FIG. 4, it shows the comparison between DNA contents detected by the flow cytometer and the mass spectra obtained from the MS test by using the equivalent cell samples, under different time points. In this example, the MS test was performed on cells harvested at 5 time points: 0 hour, 2 hours, 4 hours, 6 hours and 8 hours, and asynchronized samples acting as a control. To ensure any detected spectral differences are reproducible, 20 replicates were performed from each time point analyzed. These samples were prepared by the methods as mentioned above. As shown in FIG. 4, the mass spectra vary in response to the DNA content of the cells. The major varying region for HeLa cells locates at 7000 to around 8500 Da. There is a peak located at m/z 7000, marked with "*", increased in intensity from 0 to 2 hour and decreased in intensity from 4 to 6 hours, but increased at 8 hour finally. In addition, at mass around m/z 8500, there is a pair of peaks (marked with arrows) varying with the change in DNA content from 2n to 4n. This pair of peaks increases and decreases in strength oppositely and is therefore considered as potential marker peaks for a specific cell cycle stage of HeLa cells.

Figure 5:
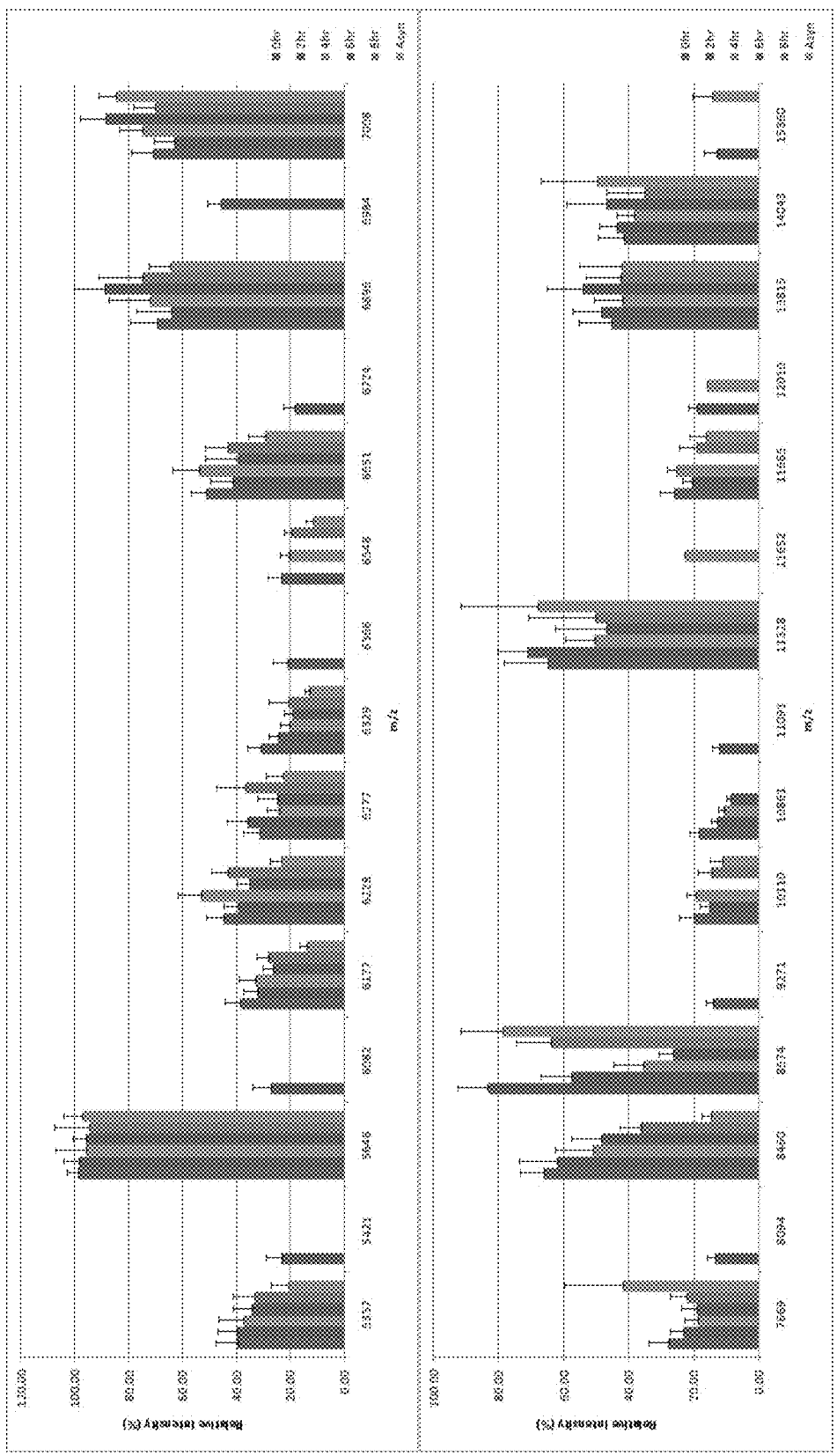
FIG. 5 shows a plot of average relative intensity of peaks of 20 replicas of 6 set of data against different time point (0, 2, 4, 6, 8 hr) and asynchronized cells converted from MALDI TOF mass spectra.

To determine whether the potential marker peak correlates to a specific cell activity or the cell cycle stage in this embodiment, the relative error of the obtained results is determined and normalization is conducted to confirm the results. In this example, average relative intensity of 20 replicas from separate time points were plotted against the mass of ions, as shown in FIG. 5. According to the 6 sets of data collected at different time points, majority of the percentage coefficient variation (% CV) of the data are ranged from 10% to 30%. FIG. 5 shows a plot of average relative intensity of peaks of 20 replicas against different time point (0, 2, 4, 6, 8 hr) and asynchronized cells converted from MALDI TOF mass spectra. With the low % CV, it is confirmed that the method of the present invention is reproducible.

In this example, the obtained mass spectra of different cell samples are then converted into quantitative vectors for normalization. Common normalization approach may be taken in this invention. For example, normalization based on relative intensity of peak height and normalization based on relative intensity of peak area. These two methods are the classical methods which represent the quantity of ions by comparing either peak height or area to the others within the same sample.

Figure 6:
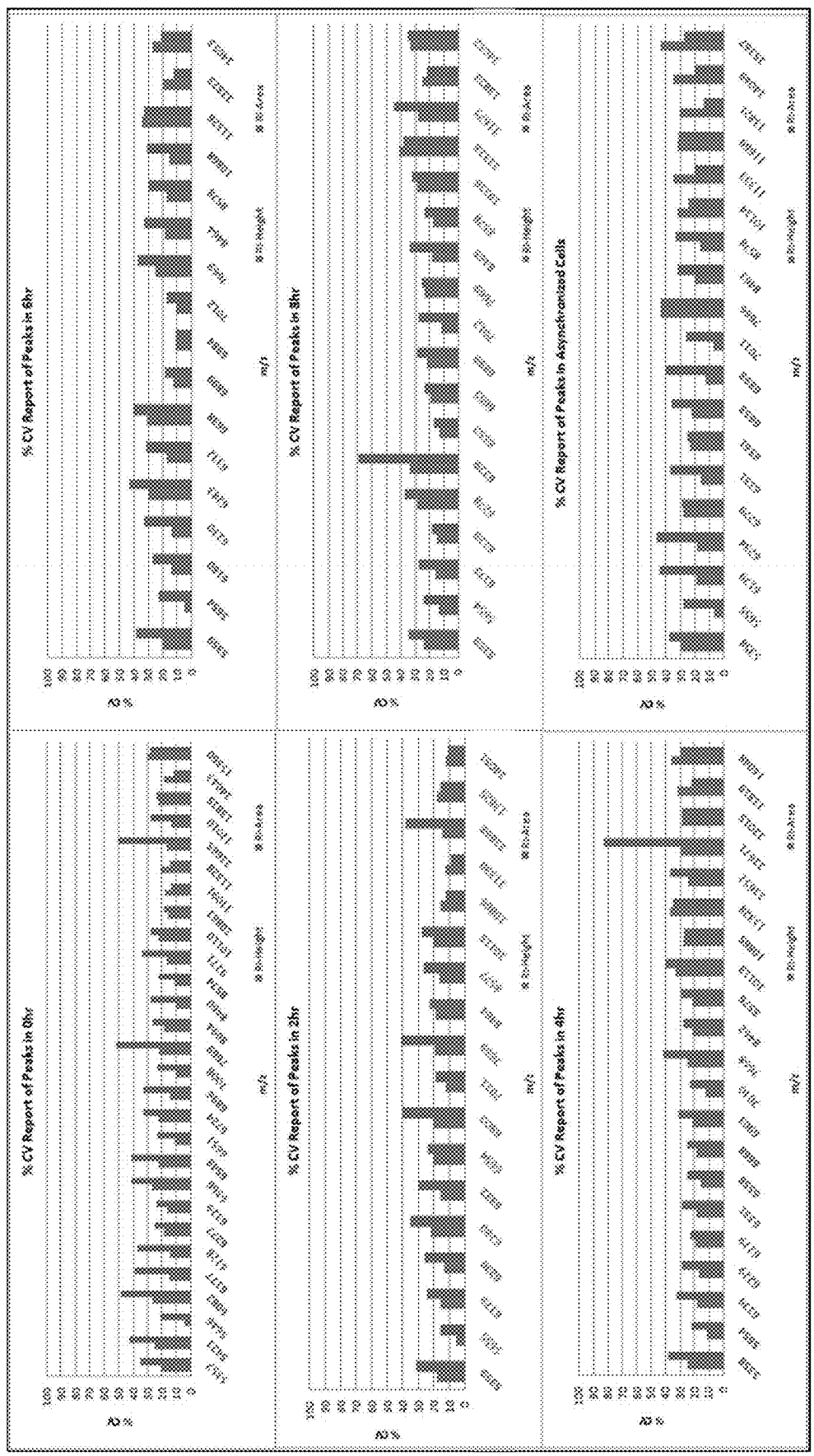
FIG. 6 shows an error analysis of relative intensity of peak height and relative intensity of peak area in one embodiment of the present invention.

FIG. 5 shows that the average relative intensity gives a range of % CV. It means that there are some errors coming from the sample preparation. In order to minimize the error arising within the samples, relative intensity of peak height and that of peak area may be used to normalize the converted data. In these two normalization methods, every peak in the samples is divided by the highest peak and largest area followed by percentage conversion. As shown in FIG. 6, the relative intensity of peak height generally provides a lower degree of error than that of peak area. Since MALDI TOF MS is a very high resolution analyzer, the peak resolution is usually very high and the peaks detected tend to form a straight line. Therefore, the relative intensity of peak height can provide a more consistent result. Regarding the relative intensity of peak height, a minor change in peak area may give rise to a larger error in peak area. It is suggested that the peak height is a more consistent and reliable tool for normalization when compared with the peak area.

In this embodiment, a new normalization approach is taken into account, which uses a factor related to a total sum of peak height of the mass spectrum. The cause of same peak giving different level of intensity in same time point was hypothesized due to the different amount of cell lysate present in different spots. Assuming the same amount of cell lysate can give certain amount of intensity, if there are fewer cell samples delivered on the sample spots, the whole spectrum will be suppressed. For example, 10 cells can give 10 unit of total peak height, and then 8 cells can only give 8 unit of total peak height. Therefore, to eliminate this error, it is necessary to expand the peaks to a certain level such that the results can provide the highest intensity for analysis. This criterion is defined by the sum of total peak height.

Preferably, a factor related to a total sum of peak height of the mass spectrum is used to normalize the data. The total sums of peak height of all samples are computed. The largest total sum of peak height among at least two converted mass spectra results of the samples is selected as the nominator of this factor for all the samples and all the peaks. The total sum of peak height of the each of the converted mass spectra results of the sample becomes the denominator of the sample. The factor is expressed as below.

$$\text{Factor in Sample 1} = \frac{\sum_{i=1}^{n}(\text{Height}_{peak_i})_{max}}{\sum_{i=1}^{n}(\text{Height}_{peak_i})_{sample_i}}$$

Figure 7:
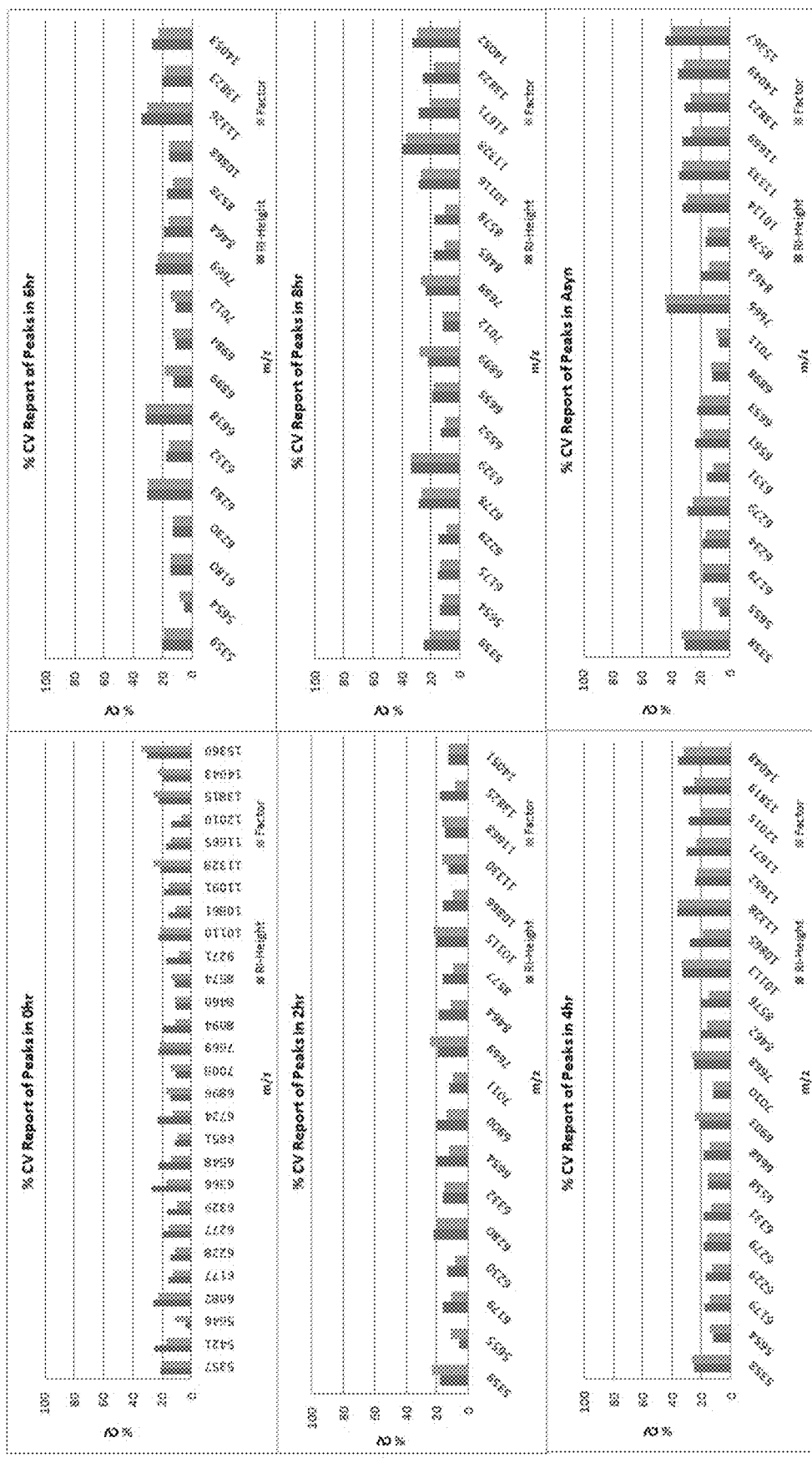
FIG. 7 shows an error analysis of relative intensity of peak height and normalization by a factor in one embodiment of the present invention.

This factor is applied to the absolute height of the peak. As a result, all the peaks are adjusted to the same level with reference to the largest total sum of peak height among all the samples. After normalization, a % CV report is done. FIG. 7 shows an error analysis of relative intensity of peak height and normalization by the factor as described above. The relative errors, resulted from the relative intensity of peak height and the factor, are generally consistent. The % CV obtained from the factor may even have a lower value. Accordingly, this factor is preferably used in the normalization of this invention.

Figure 8:
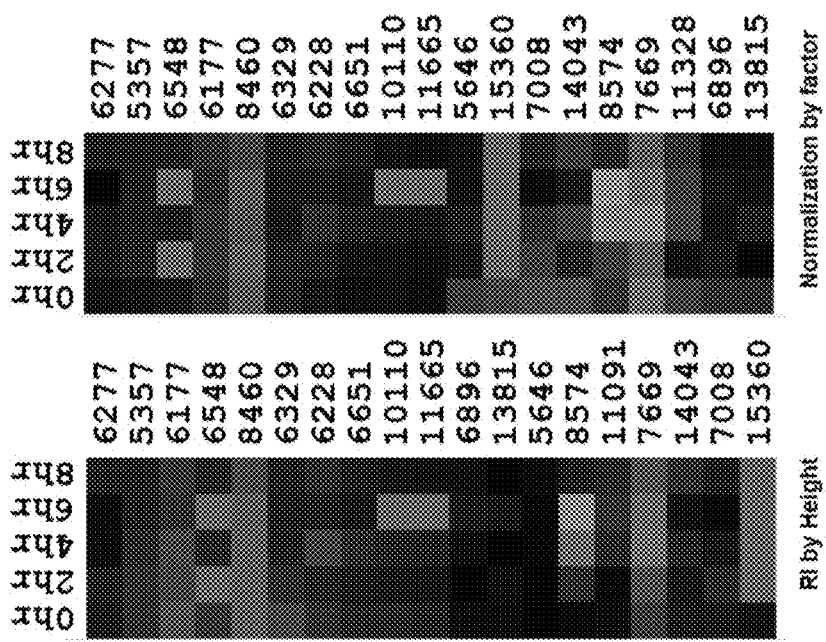
FIG. 8 shows a cluster analysis of data obtained from relative intensity of peak height and normalization by a factor.

In this embodiment, studies have been carried out to evaluate the change of peak values with respect to time. Cluster analysis may be conducted to visualize the relationship between the peak values and time. In this example, Hierarchical Clustering was done by software, Cluster 3.0 and visualized by TreeView. Data from five time points, 0, 2, 4, 6 and 8 hour were divided by that of asynchronized sample. To do with this idea, only the peaks which were present in asychronized sample were analyzed. This ratio was subjected to Binary logarithm so as to increase the sample difference. Centroid linkage clustering was done by the software. As shown in FIG. 8, the brighter the red color is, the stronger the positive relationship will be. In contrast, the brighter the green color is, the stronger the negative relationship will be. The black color represents that there is no relationship between the peak value and time, while the grey color indicates missing data. Clustering from two normalization methods resemble similar result. In both cases, peak 8460 Da and peak 8574 Da indicate a decreasing positive relationship and increasing negative relationship respectively. The data set of relative intensity of height reveals a clearer picture of these relationships. Accordingly, these two peaks 8460 Da and 8574 are confirmed to be the meaningful peaks revealing the changes in DNA content against time. In other words, the inverse relationship between these two peaks made them specific in determining the percentage of cells in a cell population, for example HeLa cells, in a specific cell cycle stage. These two peaks are therefore identified to form a ratio to serve as a biomarker providing information about the cell cycle stage distribution of the cells.

Figure 9:
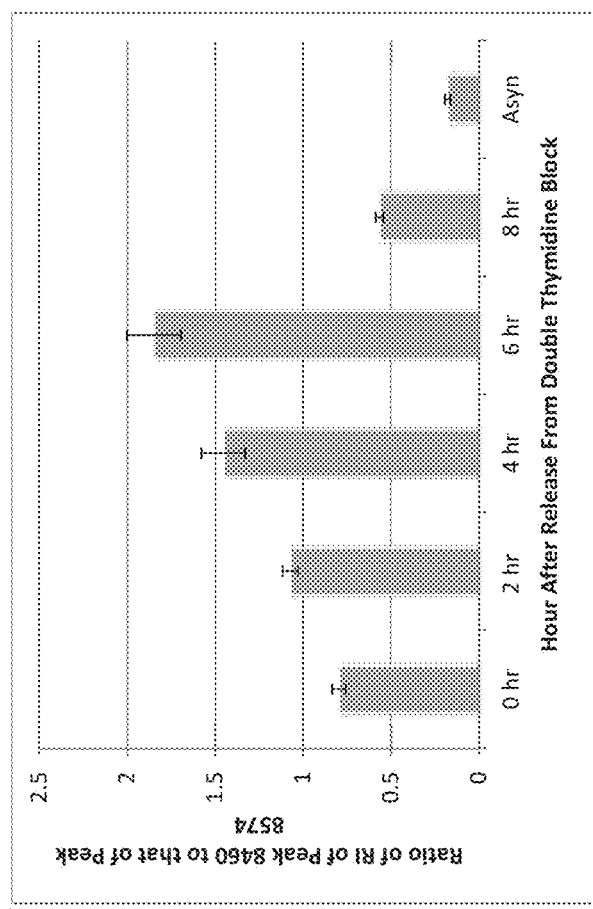
FIG. 9 shows a ratio of relative intensity of peak 8460 Da to 8574 Da at different time points after release from double thymidine block with the ratio of the asynchronized cell sample as a control.

FIG. 9 shows a ratio of relative intensity of peak 8460 Da to 8574 Da at different time points after release from double thymidine block with the ratio of the asynchronized cell sample as a control. In every sample, value of 8460 is divided by that of 8574. This ratio is very consistent and increases with time. At 6 hour after release from synchronization, it reaches the highest and it drops at 8 hour. When cells enter G1 phase, the ratio starts to increase and this increase ends at late S phase. However, in asynchronized cell this ratio does not behave as the same way as that in time=0 hour. It is suggested that this ratio is not completely coincident with the DNA content cycle. As a result, this ratio has a strong correlation to cyclic nature of cells.

As described herein, the method of the present invention is able to identify marker peaks or say characteristic peak for determining the cell cycle stage distribution of cells. The marker peak strongly correlates to a cell cycle event and thus the relationship between at least two marker peaks may provide information about the progress of a series of cell cycle events of a cell sample. Preferably, when at least two marker peaks are identified, the ratio between these two markers acts as a biomarker providing information about the cell cycle stage distribution of the cells. The present invent provides a method of identifying a biomarker for the cell cycle stage distribution of cells in a second aspect.

Generally, human cancer cell exhibit distinct MALDI TOF mass spectrum in different cell cycle stages. It reflects that MALDI TOF MS is able to report different cell activities. Accordingly, the present invention is applicable in many aspects of studies such as cell cycle study, physiological study of cells. Since MALDI TOF MS can be easily operated with only small amount of sample used, the present invention may assist in high throughput analysis of cancer cell status. This is in particular beneficial to drug development to measure a potential drug's action. In addition, different cell types express protein in a different manner, it makes a huge different in MALDI MS. The present invention can therefore be applied in cell differentiation analysis, as well as protein synthesis studies.

It should be understood that the above only illustrates and describes the preferred examples whereby the present invention may be carried out, and that modifications and/or alterations may be made thereto without departing from the spirit of the invention.

It should also be understood that certain features or steps of the invention, which are, for clarity, described in the context of separate embodiments, may also be provided in combination in a single embodiment. Conversely, various features or steps of the invention which are, for brevity, described in the context of a single embodiment, may also be provided or separately or in any suitable subcombination.

The invention claimed is:

1. A method of collecting cells at a desired cell cycle stage, the method comprising steps of:
   preparing a pre-treated cell sample by re-suspending a cell lysate of synchronized cells with purified water or pre-washing intact synchronized cells with purified water, and mixing with a matrix solution containing α-cyano-4-hydroxycinnamic acid diluted in acetonitrile or trifluoroacetic acid;
   conducting a matrix-assisted laser desorption/ionization time-of-flight mass spectrometry test for the pre-treated cell sample to obtain a mass spectrum analysis of the pre-treated cell sample and identifying a biomarker corresponding to a cell cycle stage distribution of cells in the pre-treated cell sample, wherein the biomarker comprises a pair of marker peaks having an inverse intensity relationship relative to each other over selected time points;
   performing a double thymidine block synchronization after the step of identifying the biomarker to arrest the cells in a separate cell sample at G1/S phase, and releasing the arrested cells from thymidine block to form synchronized cells; and
   collecting the synchronized cells at the selected time point which corresponds to the desired cell cycle stage, wherein the selected time points comprise 0, 2, 4, 6 and 8 hours from synchronization.

2. The method of claim 1, wherein the pair of marker peaks of HeLa cells are m/z 8574 and m/z 8460.

3. The method of claim 1, wherein the biomarker is identified by:
   generating a set of normalized data by dividing an intensity of each peak obtained from the mass spectrum analysis with a total sum of peak intensity obtained from the mass spectrum analysis; and
   identifying the pair of marker peaks from the normalized data, wherein the pair of marker peaks has an inverse intensity relationship relative to each other over selected time points; and wherein an intensity ratio of the pair of marker peaks provides information about the cell cycle stage distribution of the synchronized cells over the selected time points.

4. The method of claim 1, further comprising a step of detecting DNA content of the cell by using a flow cytometer and comparing the DNA content with the mass spectrum analysis.

5. The method of claim 1, wherein the cells are mammalian cells.

6. The method of claim 1, wherein the cells are HeLa cells.

7. The method of claim 1, wherein the selected time points consist of 0, 2, 4, 6 and 8 hours from synchronization.

* * * * *